(12) United States Patent
Korejwo

(10) Patent No.: US 7,140,843 B2
(45) Date of Patent: Nov. 28, 2006

(54) FLUID PUMP FOR MEDICAL PURPOSES AND MEASURING CHAMBER THEREFOR

(76) Inventor: Richard Korejwo, Karmellterweg 25, 13465 Berlin (DE)

(*) Notice: Subject to any disclaimer, the term of this patent is extended or adjusted under 35 U.S.C. 154(b) by 432 days.

(21) Appl. No.: 10/614,533

(22) Filed: Jul. 7, 2003

(65) Prior Publication Data
US 2004/0136839 A1    Jul. 15, 2004

(30) Foreign Application Priority Data
Jul. 5, 2002  (DE) .............................. 102 31 461

(51) Int. Cl.
*F04B 49/06*   (2006.01)
(52) U.S. Cl. ........................... 417/44.9; 604/67
(58) Field of Classification Search ........... 417/44.2, 417/44.9, 63; 604/65, 67, 151, 153
See application file for complete search history.

(56) References Cited
U.S. PATENT DOCUMENTS

| | | | |
|---|---|---|---|
| 4,838,856 A | * | 6/1989 | Mulreany et al. ............ 604/65 |
| 4,878,896 A | | 11/1989 | Garrison et al. ............. 604/65 |
| 5,429,602 A | * | 7/1995 | Hauser .................... 604/65 |
| 6,312,227 B1 | * | 11/2001 | Davis ..................... 417/45 |
| 6,488,660 B1 | * | 12/2002 | Futterknecht .............. 604/129 |
| 6,558,125 B1 | * | 5/2003 | Futterknecht ............. 417/44.9 |
| 6,817,984 B1 | * | 11/2004 | Robinson et al. .......... 604/4.01 |

FOREIGN PATENT DOCUMENTS
DE   195 25 926   11/1996

* cited by examiner

*Primary Examiner*—Michael Koczo, Jr.
(74) *Attorney, Agent, or Firm*—Young Basile

(57) ABSTRACT

Fluid pump for medicinal, especially endoscopic, applications having a transport channeled through a drive, a device possessing a measuring chamber for measuring the pressure of the fluid conveyed in the transport channel and control means for the automatic control of the behavior of the pump, in particular its transport behavior, as a function of the measured pressure and as a function of a code value contained in code value carrier means which are provided on or in the measuring chamber, wherein the code value is detected during and/or after fixing of the measuring chamber on the pump housing by read-out means in the fluid pump.

21 Claims, 6 Drawing Sheets

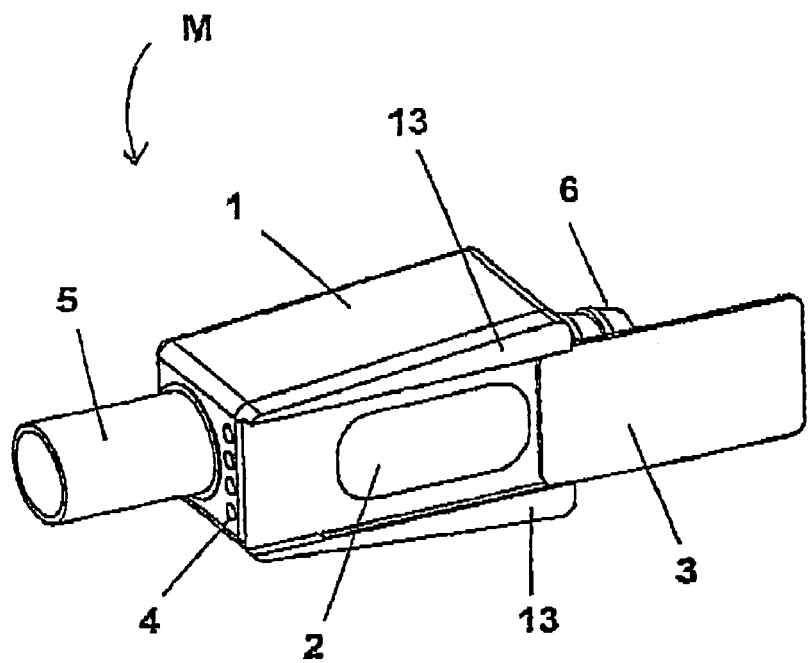
FIG. 1a
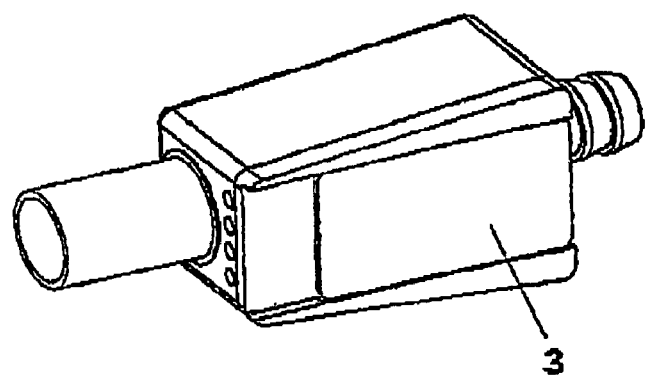
FIG. 1b

FLUID PUMP FOR MEDICAL PURPOSES AND MEASURING CHAMBER THEREFOR

The invention relates to a fluid pump and a measuring chamber.

BACKGROUND OF THE INVENTION

Patent specification DE 195 25 926 C1 discloses a peristaltic pump system in which a measuring device is inserted into the pump system hose line after the pump. This measuring device downstream of the pump determines the fluid transport volume of the pump by pressure measurement. In this case the measuring device is built up in simple manner as a block so that it can be removed from a mounting in order that the test housing can be disinfected without complication. At the same time the fluid pressure is transmitted from the interior of the test housing to the outside via openings which are covered tightly by a membrane.

In so doing the test housings can be built up of reusable measuring chambers to be disinfected, or alternatively, of single-use products packed in a sterile manner. Due, however, to the removability of the measuring chamber or the design of the measuring chamber as a separate, exchangeable accessory part, a critical and serious disadvantage, especially in the field of medicine, arises in that a measuring chamber which is actually destined and suitable for a certain first pump system is inadvertently employed in a different pump system, the result of which may be that the proper functioning of the latter pump system may be put into question.

This is especially the case, for example, when pump systems with their respective measuring chambers are on hand from different manufacturers as accessories and the measuring chambers from a first manufacturer can be inserted into the pump systems of a different manufacturer (such as when the external dimensions of the measuring chambers from the different manufacturers are identical to one another) but pressure measuring properties of the measuring chambers differ from manufacturer to manufacturer. This can cause faulty operation of the pump systems.

SUMMARY OF THE INVENTION

Accordingly, it is the object of the present invention to specify a fluid pump having a pressure measuring chamber and a pressure measuring chamber therefor which is particularly simple and robust to handle in clinical practice, for which the measuring chambers are particularly inexpensive to manufacture in industrial mass production and wherein the inadvertent use of a measuring chamber in a pump unsuitable for this measuring chamber is prevented.

These tasks are solved according to the invention by a fluid pump and a measuring chamber.

The invention exhibits the following advantageous characteristics.

Due to the fact that code value carrier means are provided on the measuring chamber of the fluid pump according to the invention, a particular advantage is achieved that code values can be entered into these code value carrier means and hence the measuring chamber can be individualized Such code values can be alphanumeric values or other values which carry information about the type and/or performance characteristics of the measuring chamber or its manufacturer. Due to the fact that during and/or after fixing of the measuring chamber on the pump housing of the fluid pump—for example by insertion into a holding device in the fluid pump—the code value carrier means can be recorded by the read-out means of the fluid pump, a particularly unpractical additional work step in the practical clinical field is avoided from the outset for example, establishing an electric cable connection between the code value carrier means and the fluid pump, or for instance the manual read-out of a scanning code applied to the housing of the measuring chamber by a manual scanner connected to the fluid pump.

Due to the fact that read-out means are provided, which can read out the code value from the code value carrier means, the fluid pump can match its operational behavior to the measuring chamber employed according to the code value entered into the code value carrier means on the measuring chamber. This matching can consist, for example, in a change in the transport behavior of the pump or preventing the pump from operating.

The ability to attache the pressure measuring chamber on to the pump housing can be achieved, for instance, by configuring the housing of the measuring chamber and the fluid pump in such a way that the measuring chamber is insertable into a holding device on the fluid pump. Thus, it is particularly easy to fit the measuring chamber into a tube line without additional fastening effort and to remove it again without appreciably increasing the length of the tube line in doing so. Such a housing design can be achieved, for instance, by providing a box-shaped housing having a smooth and robust surface which is scratch-proof and resistant to fracture, and in which fragile outer parts are avoided.

Advantageous refinements of the invention are possible according to the subsidiary claims referring back to the latter and are explained below.

The adaptation of the pump behavior is brought about by the functions of the control means of the fluid pump which control the behavior of the fluid pump as a function of the code value recorded by the read-out means and held in the code value carrier means of the measuring chamber. In this way it is possible to control the operating behavior of the pump by using different code values when using different measuring chambers having at least externally identical geometric dimensions. For instance, a first measuring chamber having a first code value can trigger the transport properties of the pump for interventions in the field of the central nervous system, and wherein a second measuring chamber having a second code value in the same fluid pump can trigger the transport properties for endoscopic interventions in the knee.

In this way erroneous use of a measuring chamber not belonging to the pump can be effectively prevented, which can prevent for example, the pressure of the transported fluid, and hence its transport flow rate, from being wrongly determined, or a measuring chamber being used in association with the fluid pump which does not meet the properties demanded and specified by the pump manufacturer.

A particularly simple implementation of the interplay of the code value carrier means of the measuring chamber and read-out means of the fluid pump is to implement the code value carrier means as one or more, for example, pin shaped profiles on the measuring chamber housing, which due to a suitably complementary profile in the pump housing, allow the measuring chamber to be attached to the pump housing only when the pattern (corresponding to the code value) formed by the pins on the measuring chamber matches that specified by the profiling of the pump housing. The fluid pump can then be implemented in such a way that it can be operated only when a measuring chamber is completely attached to it.

Other methods of implementing the control means, especially when they involve functions suitable for the purpose of electronic control, having the read-out means detect a code value from the code value carrier means and checking the code value by means of a suitable control logic circuit of the fluid pump to see whether this code value (or this number of code values) agrees with the code value(s) expected by the control logic circuit. Thus, by simply inserting a measuring chamber coded in suitable manner, the transport behavior of the fluid pump can be adapted according to the desired medicinal use or blockage of the pump can be triggered so that safe operation of the pump can be ensured.

A particularly advantageous method of implementation is when the code value carrier means contain means for optical and/or electric and/or magnetic and/or mechanical code value storage, and also means for transmitting a code value in one of the aforesaid ways insofar as these cannot be read out directly from the code value carrier means by the read-out means of the fluid pump.

In doing so the read-out means need not necessarily embody the same principle of implementation as the code value carrier means, but can be adapted to these. Thus, it is conceivable, for instance, to have mechanical code value storage by means of prominences on the housing of the measuring chamber which are detected optically, or alternatively, by mechanical scanning of a magnetic storage system.

It is particularly advantageous for the code value contained in the code value carrier means—a plurality of code values simultaneously is equally conceivable—represent information relating to the physical properties of the measuring chamber(such as flow cross-section of the transported fluid or cross section of the measuring nozzle) and/or relate to the manufacturer (measuring chamber manufacturer or fluid pump manufacturer) and/or relate to the intended mode of operation of the pump (such as desired transport volume; or permitted transport tolerance in different medicinal applications).

A practical and particularly low-cost variant for implementing the coding means is, for instance, to provide on the housing of the measuring chamber mechanically scanable prominences and/or depressions and/or excavations. This provides a low-cost and robust solution for the code value carrier means whose serviceability is not impaired by moisture and/or chemicals, radiation and heat. If the code value carrier means are arranged on one side of the measuring chamber housing so that they come into direct contact with the read-out means of the fluid pump, the scanning of the code pins can take place by means of electric pressure contacts, such as a pressure sensitive keyboard for instance. Particularly advantageous is to arrange the code value carrier means and read-out means in such a way that they are placed in effective contact with one another directly by attaching the measuring chamber on or in the housing of the fluid pump, without further action.

Other methods of implementation are also conceivable, however such as use of a barcode as the code value carrier means and a barcode reader as the read-out means of the fluid pump, as well as representing the code value in the code value carrier means by colors In these two forms of coding it is advantageous that the barcode or the colors, as an implementation of the code value carrier means, afford a very low-cost method of implementation on the part of the measuring chamber. This is important because the measuring chamber, in comparison with the fluid pump, are produced in very large numbers.

A somewhat more costly method of implementation provides for an integrated circuit as the code value, carrier means in which circuit. At least one code value is stored in the integrated circuit. This method is advantageous in that the number of code values, or the information contained in the code value, can be much more extensive. A particularly advantageous method of implementation is to transmit the code value from the code value carrier means to the read-out means by electromagnetic signals.

With regard to the practical clinical use of the measuring chambers, it is particularly advantageous to provide the housing of the measuring chamber with means for the unique identification of the orientation of the housing relative to the fluid pump housing. When attaching the measuring chamber on or in the pump, for example, in a holding device provided for this purpose on or in the pump and by a translational movement of the measuring chamber in the longitudinal direction of the measuring chamber housing, this is a simple way of preventing the measuring chamber from being inserted the wrong way round, in particular with the chamber connected counter to the planned direction of flow in the tubing circuit. By providing such means the user need not take any particular care when inserting the measuring chamber. For example, the attaching means can take the form of a special shape for the housing that compliments the shape on the fluid pump, such as, for instance, the use of asymmetric geometric features for the housing geometries.

A further advantageous refinement of the measuring chamber provides for a membrane on the measuring chamber onto which the pressure from the interior of the measuring chamber can be transmitted through openings provided for this purpose in the measuring chamber housing. The openings are tightly covered by the membrane and the leak-proofness of the membrane prevents the transported fluid from escaping a closed system within the measuring chamber.

In combination with the membrane, and in particular with regard to practical use, it is advantageous to equip the measuring chamber with a membrane protector completely covering the membrane, by which means the membrane is reliably protected on the measuring chamber in practical use, such as transport or disinfection, and unintended tearing or bulging of the membrane is prevented. It is particularly advantageous for the membrane protector to be opened by lateral displacement along the measuring chamber housing.

For example, the membrane protector can be constructed in such a way that when affixing the measuring chamber to the fluid pump the membrane protector automatically opens to expose the membrane and allow the fluid pump contact with the membrane, such as by fluid sensors in the fluid pump for instance. This in particular avoids the disadvantage of a sheath-like or hood-like cover, which must be put in position or removed with some effort by hand and can easily be lost. In a manner analogous to the automatic opening of the membrane protector upon attaching the measuring chamber to the pump, the membrane protector can be closed upon removal of the measuring chamber from the fluid pump.

A particularly practical embodiment for the lateral displaceability of the membrane protector constructed as a plate takes the form of guide rails positioned along the measuring chamber housing which can be implemented as moldings on the measuring chamber housing. By means of the automatic opening and closing of the membrane protector on the measuring chamber when it is fixed on or in the fluid pump there is no need for unwieldy manual pushing aside or removal of the membrane protector or putting it back on which might require the user to use both hands.

Another advantageous embodiment of the measuring chamber provides for locking means on the measuring chamber which hold the housing by friction fitting and/or form fitting after it is fixed on a fluid pump. The means of engagement as preferably constructed in such a way that on fixing they produce a clearly perceptible click and fixing and removal can be effected by simple and direct application of translational force, in particular without operation of additional unlocking devices.

It is, furthermore, advantageous to provide a pump segment which is fixedly connected by clamping to the measuring chamber on the inlet side. This has the advantage that on each change of measuring chamber this pump segment is also exchanged. This is of particular importance when the drive of the fluid pump constructed as a peristaltic pump is implemented via a roller wheel. Particularly high demands are imposed on the mechanical properties of the pump segment, which is constructed as a flexible tube. These mechanical properties of the pump segment are subject, however, to particularly marked ageing or attrition during use so that regular replacement is required. In the present embodiment this is ensured by the fixed attachment of the pump segment to the measuring chamber.

Another advantageous embodiment provides for a flow channel in the measuring chamber, and the construction therein of a measuring nozzle reducing the flow cross-section of the fluid streaming through the flow channel, wherein ahead of and following the measuring nozzle openings are arranged for externalizing the measuring chamber which allow measurement of the pressure.

The characteristics of the invention exhibit the following advantageous effects.

Due to the fact that the measuring chamber includes a code value carrier means in which at least one code value is present, and includes means for code value storage and transmission to enable the code value to be retrieved in simple manne, the measuring chamber can be individualized and the compatibility of measuring chambers with fluid pumps from different manufacturers can be selectively controlled as described above in more detail. Compatibility and individualization can be provided in this manner without the need for producing differences in the housing or in the mechanically fitted shape which are costly in production terms. By this means the effects of scale in large-scale industrial production are exploited since housing production for all measuring chambers can ensue in the same way according to external dimensions and in this way standardization effects in production arise.

Advantageous refinement of the invention is possible according to the refinements of the fluid pump relating to the measuring chambers.

BRIEF DESCRIPTION OF THE DRAWINGS

The invention is explained below with reference to an exemplified embodiment. The drawings show:

FIGS. 1a and 1b show a wedge-shaped measuring chamber with a membrane in which the membrane protector is in the open and closed state, respectively, and having code value carrier means in the form of code pins;

DETAILED DESCRIPTION OF THE PREFERRED EMBODIMENT

Figure 2A:
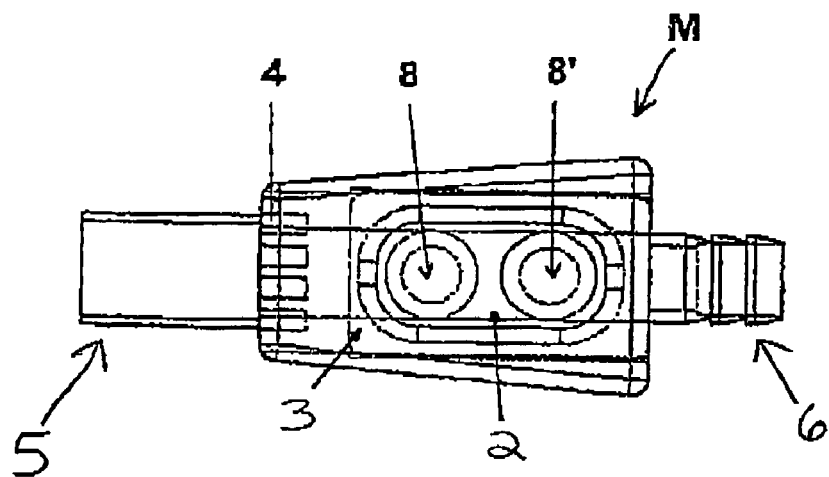
FIGS. 2a–2c show a cut-away view of the measuring chamber from the side of the housing opposite the membrane, a view at right angles to the membrane side, and a view of the membrane side, respectively.

FIGS. 1a and 1b shown an exemplified embodiment of a measuring chamber according to the invention. The measuring chamber has a block-like housing 1 with a level surface. On one end face of the block-like housing 1 a pump segment 5 is clamped in place, and inserted into the other end face is a tube connection 6, which together form an extension of a flow channel 7, not illustrated in more detail in this figure. In accordance with the invention, and as described later in association with FIGS. 3 and 4, the measuring chamber, or the housing 1, is pushed into a mounting, which at present is not necessarily fastened to a pump.

Likewise on the end face of the housing 1 accommodating the pump segment 5, there are located code value carrier means 4 implemented in the form of code pins.

These code pins contain a code value which, for example, contains the name of the company which produced the measuring chamber and the cross-section of the flow channel in codified form. The code pins 4 are located on the end of the measuring chamber facing the plug-in direction of the measuring chamber when inserting the measuring chamber into a holding device on the fluid pump. In this special case, but not generally, the plug-in direction is the side from which the fluid flows into the measuring chamber.

Figure 2B:
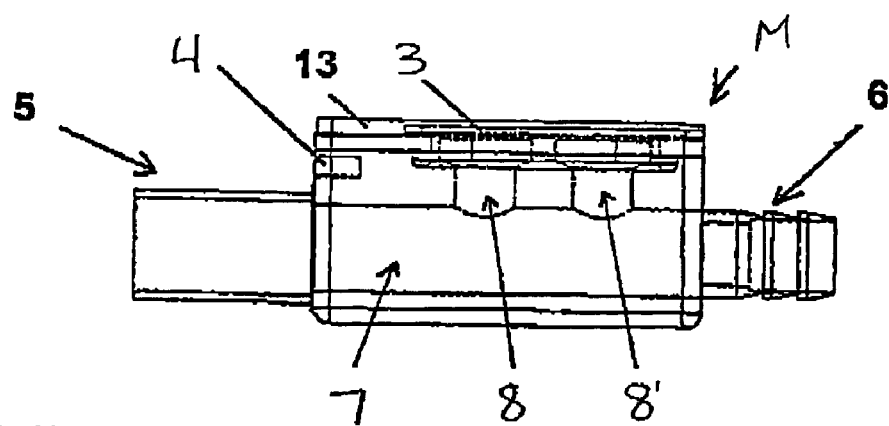
Figure 2C:
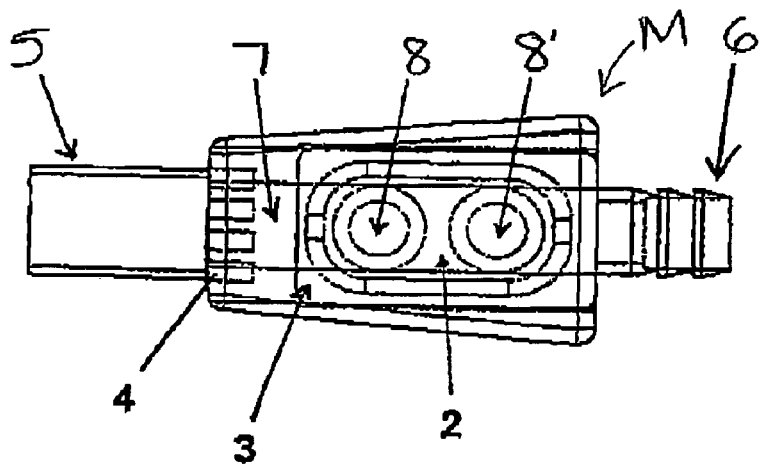

Referring also to FIGS. 2a–2c, membrane 2 can also be seen, which covers openings 8 and 8' between the flow channel and the outside of the measuring chamber. A membrane protector 3 is constructed in the form of a plate which is displaceable to the side, and is guided in stable and secure manner to prevent it slipping out by guide rails 13 projecting from the housing along the sides of membrane protector plate 3, FIG. 1a shows the membrane protector 3 in the open state, and FIG. 1b the measuring chamber with the membrane protector 3 in the closed state. Membrane protector 3 will normally be in the closed position, as shown in FIG. 1b, when handling the measuring chamber while removed from the holding device of a fluid pump A return structure can be provided in the housing I which ensures that, absent a lateral displacement force, the membrane protector 3 always returns to the basic closed state as depicted in FIG. 1b.

FIGS. 2a–2c show the same measuring chamber shown in FIGS. 1a and 1b in cut-away from the side (FIG. 1a) located opposite the membrane, in cut-away perpendicular to the membrane side (fig 1b), and from the membrane side (FIG. 1c).

In FIG. 2a the pump segment 5 can be seen in the way it is plugged into the inlet of a flow channel 7. A flow outlet in the form of the tube connector 6 is also clearly visible. FIG. 2a shows how the membrane surface 2, illustrated by the continuous line of the rounded rectangle surrounding the area 2, covers the openings 8 and 8' illustrated as the interior of the dotted rings located therein. Located above this is the membrane protector 3, which is illustrated by a dotted line. Likewise, illustrated by dotted lines are the code pins 4 in one end faces of the housing.

The view in FIG. 2b, tuned with respect to FIG. 2a by 90° in the horizontal plane, shows the membrane protector 3 in the guide rails 13. The guide rails 13 extend to the right outside edge of the measuring chamber so that the membrane protector can be pushed to the right beyond the boundary of the measuring chamber housing. In this view the openings 8 and 8' are also clearly visible, which connect the inside of the membrane 2 (not illustrated in more devil in FIG. 2b to the flow channel 7.

FIG. 2c shows the closed membrane protector 3 as a continuous line. Located behind the membrane protector, and shown in dotted lines, is the membrane 2 and the openings 8 and 8' that lead to the flow channel 7. It also shows how the membrane protector 3 is held in the guide rails 13. Where the continuous line of the membrane protector plate 3 passes behind the likewise continuous projection overlapping the plate 3 at top and bottom, the continuous line of the membrane protector 3 transitions into a dotted line.

A measuring nozzle located between the openings 8 and 8' in the flow channel 7 is not illustrated in more detail, but is readily imaginable, especially in the view in FIG. 2b between the openings 8 and 8', as a tapering of the flow channel 7.

Figure 3:
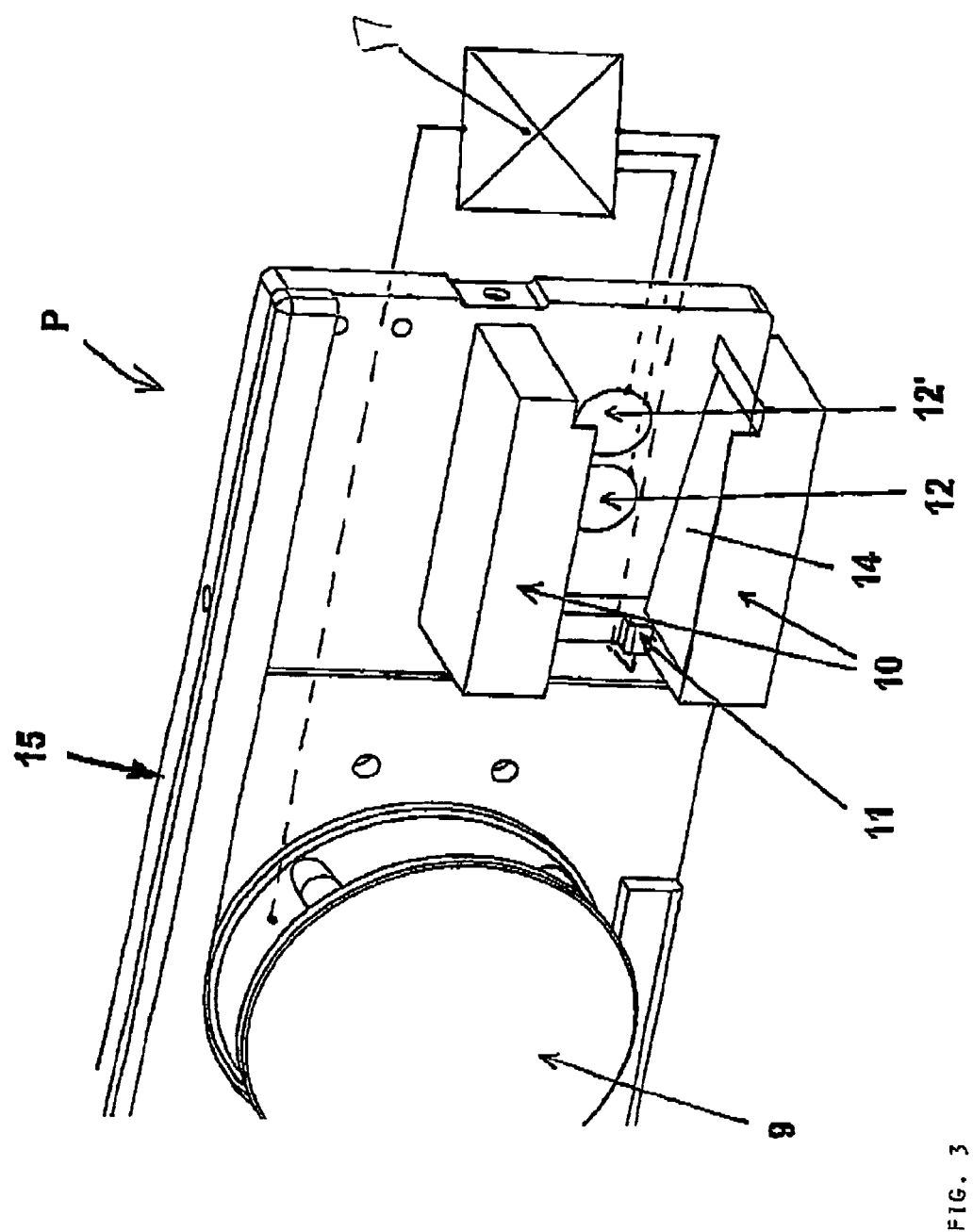
FIG. 3 shows a fluid pump constructed in the form of a peristaltic pump having a roller wheel and holding device for accommodating the measuring chamber pushed in from the side.

FIG. 3 shows an exemplified embodiment of a fluid pump according to the invention, constructed in the form of a peristaltic pump, which in the present case is designed to accommodate the measuring chamber as implemented in the exemplified embodiment in FIGS. 1 and 2 described above, so that the fluid pump and measuring chamber are actively connected according to the invention.

Other forms of fluid pumps of providing similar means for connecting to the measuring chamber may contain a drive based on the peristaltic principle but without a roller wheel for producing the peristaltic effect or, furthermore, a drive based on a rotor or impeller driven by magnetism and may also be arranged in the axial direction relative to the transport channel. A design in the form of a gear-type pup having a closed gear chamber is also conceivable.

In the present exemplified embodiment in the form of a peristaltic pump, the housing 15 has a roller wheel 9 around which a flexible tube can be placed and measuring chamber can be attached to the holding device 10. Accordingly, the transport channel is constructed as a tube line.

The holding devices 10 are configured as moldings on the pump housing and formed in such a way that they completely accommodate securely encompass the block-like housing 1 of the measuring chamber. The measuring chamber has a prismatic construction with a trapezoidal outline on the membrane side. Accordingly, the holding device 10 have sloping guide surfaces 14 which engage with the sloping side surfaces of the measuring chamber housing.

Positioned at the end of the holding device 10, viewed in the insert direction, is at least one read-out means constructed as a reading contact 11, which is arranged to work together with the code pins 4. The at least one reading contact 11 and code pins 4 may also have different embodiments, and may be implemented in a mechanical, for example pins and holes engaging one another, electrical, and/or optical manner.

Through mechanical scanning of the corresponding code pin 4 of the measuring chamber, the reading contact 11 is able to read out the single-place code value located therein. In this example, it is checked whether the measuring chamber to be inserted in the mounting 10 is compatible with the pump.

The housing 15 of the pump is provided with pressure sensors 12 and 12', which work together with the measuring chamber. The pressure sensors 12 and 12' are arranged in such a way that when the measuring chamber is inserted into the mounting 10 the pressure sensors are placed in direct active contact with the membrane 2, which is exposed from under its membrane protector 3 when the the measuring chamber is completely pushed in and locked in place in the mounting 10. With the measuring chamber attached to the mounting 10, the pressure sensors 12 and 12' are located directly opposite the region of the openings 8 and 8'. Locking means, which are not illustrated, are provided for locking the measuring chamber to the holding device 10. The locking means are fitted on the holding device 10 and/or the housing 1 of the measuring chamber.

The presence of only one read-out means 11, for example, a mechanical scanner for only one code pin, serves only to improve the clarity of presentation. A plurality of read-out means can of course be present, which can advantageously be arranged (as in the implementation of a strip scanner) one above the other in a row as suggested in the illustration of the code pins 4 in FIG. 1a.

Figure 4:
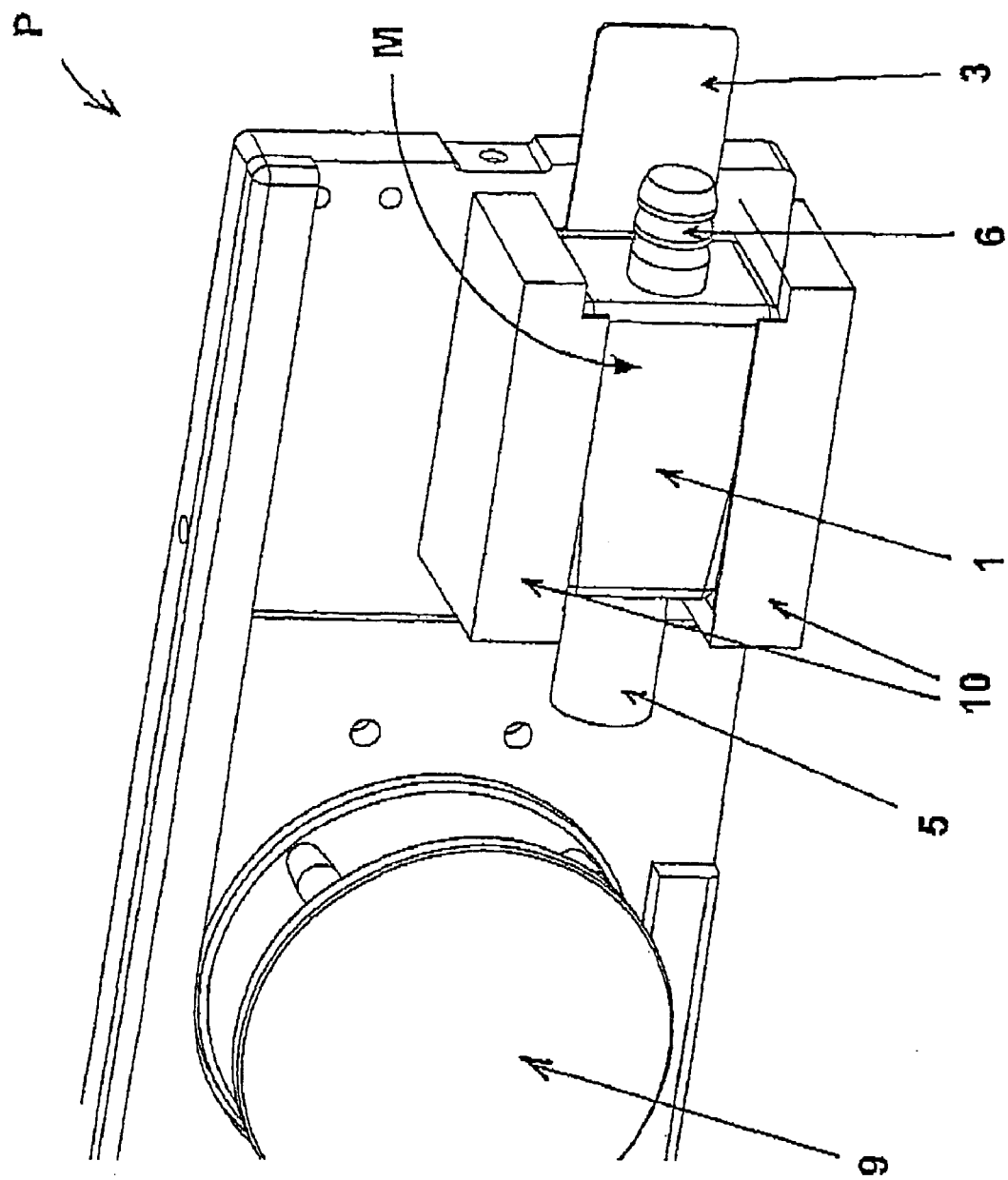
FIG. 4 shows the fluid pump illustrated in FIG. 3 with the measuring chamber illustrated in FIGS. 1 and 2 shown inserted and locked to the fluid pump.

FIG. 4 shows the fluid pump illustrated in FIG. 3 with the measuring chamber inserted and locked in position, as illustrated in FIG. 1a. At the start of the insertion operation the membrane protector 3 is caught by a catch, which is not illustrated in more detail, at the level of the pressure sensors 12 and 12', and held so that the membrane 2 on the measuring chamber is exposed as the insert movement continues. Once the measuring chambers is fully inserted and locked in place, the reading means 11 makes contact with the code value carrier means 4 so that a control means 17 in the system, which may also contain a means for determining the transport volume from the signals of the pressure sensors, determine whether the system is ready for operation and/or in which way the system operates. At the same time the pressure sensors are in active contact via the membrane 2 with the openings 8 and 8'.

If the measuring chamber is equipped with a suitable return device then, upon unlocking and removing the measuring chamber from the holding device 10 on the fluid pump, the membrane protector 3 advances again over the membrane to protect the membrane without any action by the user. From here the measuring chamber can be collected and disinfected without any special care, which proves to be advantageous especially in practical clinical operations.

Figure 5:
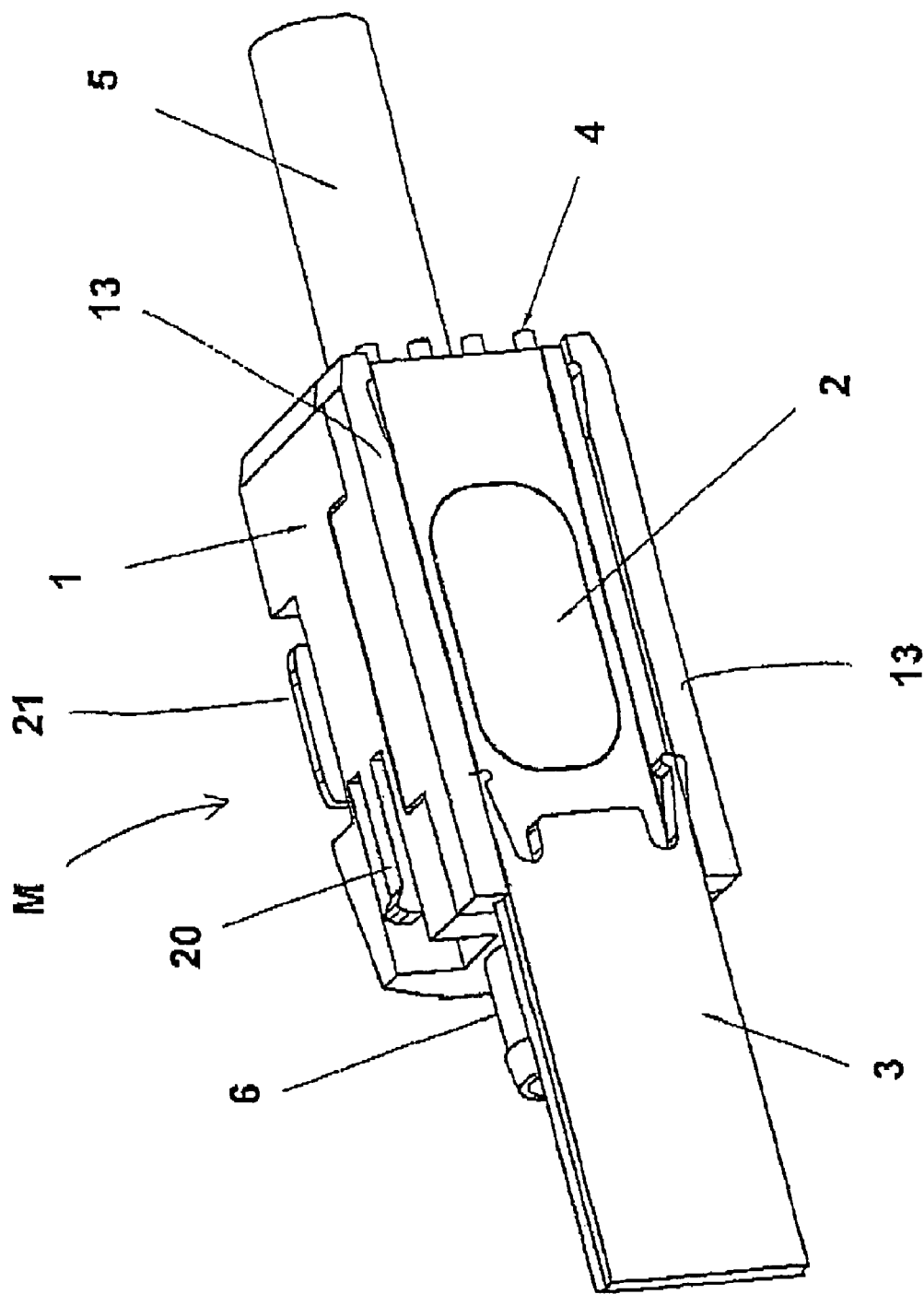
FIG. 5 shows a detailed version of the measuring chamber shown in FIG. 1 with guide rails and locking means, wherein in this case the housing shape is a parallelepiped.

FIG. 5 shows a more detailed version of the measuring chamber shown in FIGS. 1a and 1b, wherein recesses are provided at the right-hand end of guide rails 13 that are engageable with correspondingly shaped right-hand ends of the membrane protector plate 3 in friction fitting manner for securing the position of the membrane protector relative to the body of the measuring chamber.

Also illustrated in FIG. 5 are the code value carrier means 4 constructed as code pins, which here take the form of convex, pin-like protruberances on the housing. An engaging means 20 is located on the top or bottom of the measuring chamber housing, which upon attaching the measuring chamber on or in the housing of the fluid pump engage with a clearly perceptible click to-secure the measuring chamber in a friction fitting manner against inadvertent detachment from the fluid pump. The measuring chamber housing further includes an elastic attachment 21 which positions the measuring chamber securely inside the mounting device 10 upon insertion in the holding device. The elastic attachment 21 pushes the measuring chamber located in the mounting toward the sensors to prevent-unintended movement of the measuring chamber housing relative to the fluid pump.

Figure 6:
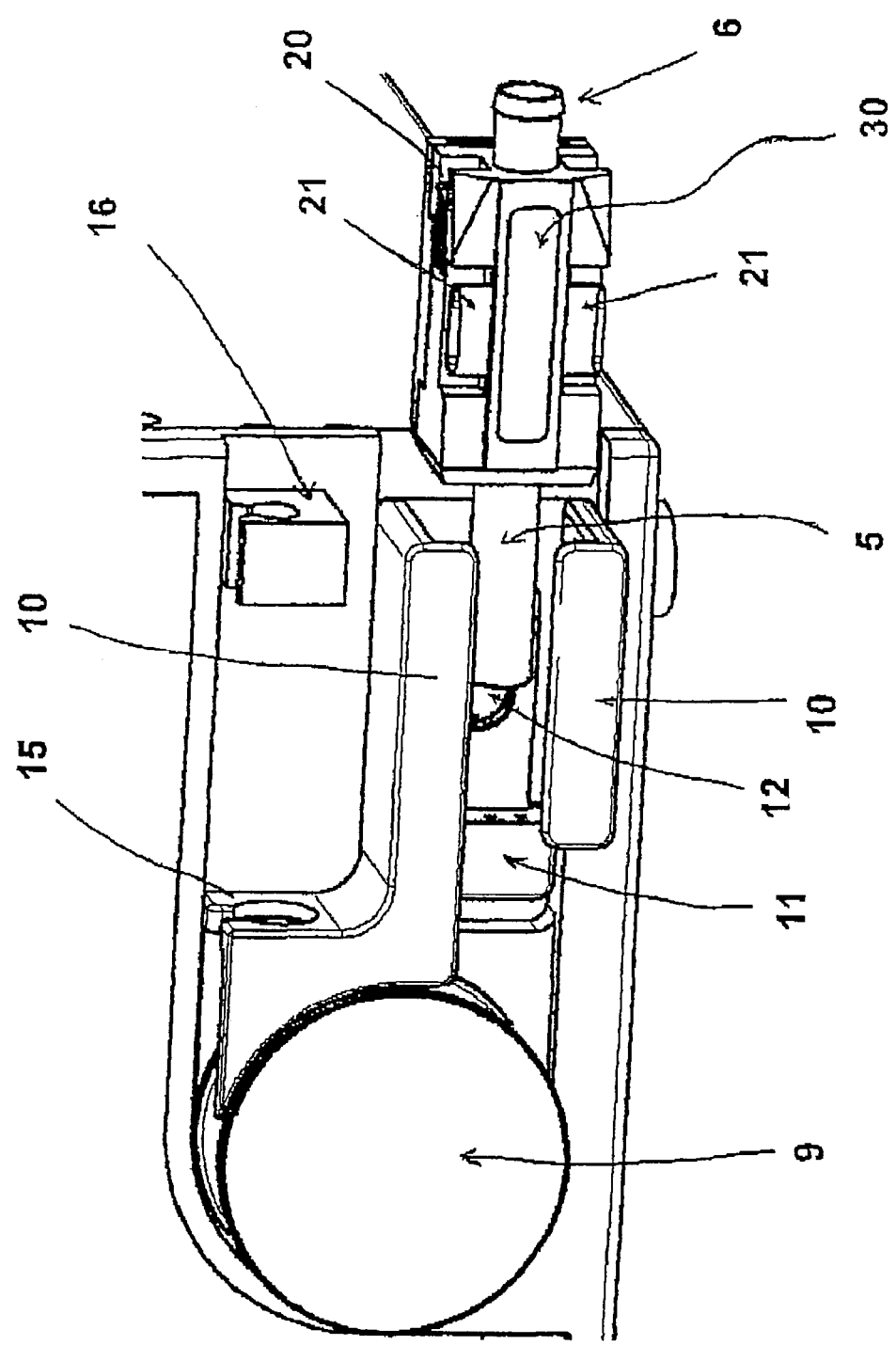
FIG. 6 shows a detailed version of the fluid pump shown in FIG. 4, showing guidance of the pump segment on insertion and stabilization of the measuring chamber.

FIG. 6 shows how attachment of the measuring chamber to a fluid pump implemented in the form of a peristaltic pump can be carried out.

Brought into the position with respect to the pump, the pump segment 5, which in this figure is shown merely as a short length, but in reality is many times longer, can be gripped by one hand while at the same time the moving the measuring chamber housing connected to the pump segment 5 into the holding device 10 by pulling in the direction of the roller wheel 9. In the course of this movement the person operating the instrument can guide the pump segment 5 clockwise round the roller wheel 9 into the holding device 15 and finally clamp the pump segment 5 in a locking device 16. In this way the pump segment 5 is fixed in a stable position and the measuring chamber is fitted securely into the holding device.

The elastic attachments 21 ensure that the measuring chamber is pressed against the pressure sensors 12 and 12' for the measuring chamber and prevent unintended slippage, while the locking means 20 produce a clearly perceptible click on engagement as soon as the measuring chamber reaches the fixed position of operational readiness on the fluid pump and further secure the measuring chamber against unintended slippage out of the holding device 11.

Another characteristic of the measuring chamber illustrated in this figure is that it has a label surface 30 for holding information, such as a label bearing the logo of the manufacturer, or other information, for example the field of use of the pump, such as "Only for uteroscopy" for instance.

What is claimed is:

1. Fluid pump for medicinal, especially endoscopic, applications having a housing, a transport channel conveyed via a drive, a device possessing a measuring chamber for measuring the pressure of the fluid conveyed in the transport channel and control means for the automatic control of the transport properties as a function of the measured pressure, wherein the measuring chamber is fixable to the pump housing, characterised in that the measuring chamber is equipped with code value carrier means containing a code value, and read-out means for registering the code value with respect to fixing of the measuring chamber to the pump housing.

2. Fluid pump according to claim 1, characterised in that the control means contain functions for controlling the behaviour of the pump as a function of the code value read out.

3. Fluid pump according to claim 2, characterised in that the behavior of the pump controlled as a function of the code value comprises the control of the transport properties of the pump as a function of the measured pressure.

4. Fluid pump according to claim 1, characterised in that the transport function of the pump is blockable as a function of the code value read out.

5. Fluid pump according to claim 1, characterised in that the code value carrier means are constructed by a means selected from a group consisting of optical means, electrical means, magnetic means and mechanical means and any combination-thereof and the read-out means are adapted to the letter.

6. Fluid pump according to claim 1, characterised in that the code value contained in the code value carrier means represents information relating to predetermined physical properties.

7. Fluid pump according to claim 1, characterised in that the read-out means contain electric pressure contacts.

8. Fluid pump according to claim 1, characterised in that the code value carrier means contain features selected from a group consisting of prominences and depressions and any combination thereof on the surface of the measuring chamber representing the at least one single code value.

9. Fluid pump according to claim 1, characterised in that the measuring chamber has a housing having means for the unambiguous identification of the spatial orientation of the measuring chamber relative to the pump housing.

10. Fluid pump according to claim 1, characterised in that the measuring chamber possesses a flow channel which is provided with at least one opening to the outside sealed by a membrane and that opposite the opening at least one pressure sensor actively connected to the membrane is arranged in the pump housing.

11. Fluid pump according to claim 10, characterised in that the measuring chamber has a displaceable membrane protector which covers the membrane.

12. Fluid pump according to claim 11, characterised in that the membrane protector comprises a plate covering the membrane at least in the region of the openings and running in guide rails.

13. Fluid pump according to claim 1, characterised in that the measuring chamber and the pump housing possess locking means which hold the measuring chamber by of a means selected from a group consisting of friction fitting and form fitting and any combination thereof after the measuring chamber is fixed on the pump housing.

14. Fluid pump according to claim 1, characterised in that the measuring chamber has a flow channel and a pump segment is provided which is clamped into the flow channel on the inlet side.

15. Fluid pump according to claim 1, characterised in that the measuring chamber has a flow channel and therein a measuring nozzle reducing the flow cross-section of the fluid flowing through the flow channel is provided, wherein an opening is arranged ahead of and an opening after the measuring nozzle in the flow channel.

16. Measuring chamber suitable for a fluid pump according to claim 1, having a housing enclosing a flow channel, characterised in that it is equipped with code value carrier means in which a code value is contained.

17. Measuring chamber according to claim 16, characterised in that the code value carrier means are constructed by a means selected from a group consisting of optical, electric, magnetic and mechanical means.

18. Measuring chamber according to claim 16, characterised in that the code value carrier means contain at least single code value representing at least one of prominences and depressions on the surface of the housing.

19. Measuring chamber according to claim 16, characterised in that the code value contained in the code value contained in the code value carrier means represents information relating to properties wherein the properties are selected from a group consisting of the measuring chamber, the geometric dimensions of the interior of the measuring chamber and the exterior of the measuring chamber relating to the manufacturer and relating to the intended medicinal field of application.

20. The fluid pump of claim 1, wherein the measuring chamber is fixed on the pump housing and the read-out means is on the pump housing and the code value is registered when the measuring chamber is fixed at the pump housing and during the operation of the pump.

21. The fluid pump of claim 6, wherein the information relating to predetermined physical properties is selected from the group consisting of relating to the measuring chamber, the manufacturer, and the intended mode of operation of the pump and any combination thereof.

* * * * *